United States Patent [19]

Tsuruoka et al.

[11] Patent Number: 4,872,335

[45] Date of Patent: Oct. 10, 1989

[54] VIBRATING TYPE TRANSDUCER

[75] Inventors: Michihiko Tsuruoka; Wataru Nakagawa; Noriomi Miyoshi; Naohiro Konosu; Tadao Hashimoto, all of Kanagawa, Japan

[73] Assignee: Fuji Electric Co., Ltd., Kanagawa, Japan

[21] Appl. No.: 922,694

[22] Filed: Oct. 24, 1986

[30] Foreign Application Priority Data

Oct. 25, 1985 [JP] Japan .................. 60-239228
Nov. 11, 1985 [JP] Japan .................. 60-252424
Nov. 18, 1985 [JP] Japan .................. 60-258130
Feb. 24, 1986 [JP] Japan .................. 61-38906
Jun. 16, 1986 [JP] Japan .................. 61-139786

[51] Int. Cl.$^4$ .................. G01L 9/08; H04R 17/00
[52] U.S. Cl. .................. 73/30; 73/32 A; 73/579; 73/571
[58] Field of Search ........... 73/30, 32 A, 579, 702, 73/24

[56] References Cited

U.S. PATENT DOCUMENTS

| | | | |
|---|---|---|---|
| 3,276,535 | 10/1966 | Shaw | 73/579 |
| 3,295,360 | 1/1967 | Dimeff | 73/30 |
| 3,456,508 | 7/1969 | Frische | 73/702 |
| 3,555,880 | 1/1971 | Menius, Jr. et al. | 73/32 A |
| 3,792,204 | 2/1974 | Murayama et al. | 73/DIG. 4 |
| 4,098,133 | 7/1978 | Frische et al. | 73/702 |
| 4,292,850 | 10/1981 | Bachem | 73/702 |
| 4,297,872 | 11/1981 | Ikeda et al. | 73/32 A |
| 4,395,908 | 8/1983 | Shopland | 73/516 LM |
| 4,435,986 | 3/1984 | Choffat | 73/702 |
| 4,631,436 | 12/1986 | Edinger et al. | 310/322 |

FOREIGN PATENT DOCUMENTS 0638858 12/1978 U.S.S.R. .................. 73/702
2087558 5/1982 United Kingdom .

OTHER PUBLICATIONS

Ernest Bose. Fluid Pressure Transducers, Nov. 1981, p. 169.

*Primary Examiner*—Stewart J. Levy
*Assistant Examiner*—Laurence G. Fess
*Attorney, Agent, or Firm*—Finnegan, Henderson, Farabow, Garrett & Dunner

[57] ABSTRACT

A vibrating transducer for detecting the resonant frequency of a vibrating diaphragm and using that frequency to determine the pressure or density of a fluid contacting the diaphragm. The device includes a container having a diaphragm separating the cavity in the container into two chambers with the diaphragm preventing flow communication between the two chambers. A first fluid inlet in flow communication with the first chamber introduces fluid to the first chamber with that first chamber having an acoustic compliance less than the mechanical compliance of the diaphragm. The second fluid input is in flow communication with the second chamber and introduces fluid into the second chamber. By controlling the acoustic compliance of the chamber with respect to the diaphragm accurate measurements of the density or pressure of the fluid can be obtained.

3 Claims, 9 Drawing Sheets

VIBRATING TYPE TRANSDUCER

FIELD OF THE INVENTION

The present invention relates to a device for detecting the resonant frequency of a vibrating solid member to measure the density or pressure of a fluid- in contact with both sides of the solid member.

BACKGROUND OF THE INVENTION

A conventional vibrating type transducer for measuring the density of a fluid on the basis of the resonant frequency of a vibrator is shown in FIG. 1 as it is disclosed in U.S. Pat. No. 3,677,067. In FIG. 1, a measuring tube 1 is arranged within a fluid channel in which a fluid being monitored flows in the direction of G. The measuring tube 1 is normally arranged that its axial direction conforms to a direction of flow. A vibrator, in the form of a rectangular plate having edges on both sides fixed to the inner surface of the measuring tube 1 to include its central axis is fixed to one end of a cylindrical body 5 whose central axis is perpendicular to the surface of the vibrator 4. A cylindrical connecting case 6 is fixed to the other end of the body 5. The cylindrical body 5 is provided with a threaded portion 3 for fitting the measuring tube 1 into the fluid channel in the manner above described. The vibrator 4 is made to promote self-excited flexural vibration resulting from arcuate bending of the edges not fixed to the measuring tube 1 by means of a mechanism (not shown), so that the vibrator 4 vibrates at the resonant frequency (Fn) of the vibrating system including the vibrator 4. When the measuring tube 1 is arranged in the fluid channel, the fluid being monitored is passed through the measuring tube 1 and the fluid in contact with the vibrator 4 is also caused to vibrate as the vibrator 4 experiences flexural vibration. The mass of the vibrating system including the vibrator 4 increases to the extent of the mass of the fluid being monitored when the fluid vibrates because of the vibrator 4. As a consequence, the value of the above resonant frequency (Fn) is different from that when the fluid is not in contact with the vibrator 4. The resonant frequency (Fn) is expressed by Eq. (1).

$$Fn = \tfrac{1}{2}\pi \cdot \sqrt{K/M + Ml} \qquad (1)$$

where M=mass of vibrator 4; K=spring constant; and M1=mass of fluid as the above additional mass.

K, M in Eq. (1) are constants independent of the properties of the fluid, whereas Ml corresponds to the density of the fluid. As is apparent from Eq. (1), the density of the fluid can be measured by monitoring the frequency of vibration (Fn). The device shown in FIG. 1 is arranged so that the density can thus be measured and the relation of the density $\rho$ of the fluid to Fn conceptually becomes what is shown in FIG. 2.

In FIG. 2, Fno represents a value of Fn when $\rho=0$, i.e., when the vibrator 4 is within a vacuum. When the fluid being monitored is a qas, the mass Ml of the qas vibrating as the vibrator 4 vibrates is significantly smaller than that of the vibrator 4. Because a gas has compressive properties and a low density $\rho$ the slope of the plot of Fn versus $\rho$ is very small. It is consequently difficult to measure the density of gas by means of the density measuring instrument shown in FIG. 1 because the frequency change corresponding to the density change is insufficient. Another problem is that the temperature range applicable to the density measuring instrument is narrow because the frequency (Fn) fluctuates as a result of changes in the dimensions of the vibrator 4. When the ambient temperature changes become greater than the change of the frequency (Fn) corresponding to the change of the density of the gas this effect cannot be disregarded, provided that the ambient temperature changes sharply The present invention is intended to solve the above problems inherent in such conventional devices, specifically it is therefore an object of the invention to provide a vibrating type transducer capable of accurately checking a low density fluid such as gas having compressive properties over a wide range of measuring temperatures.

SUMMARY OF THE INVENTION

In order to achieve the above-noted objects, there is provided a device for detecting the resonant frequency of a diaphragm to measure the properties of a fluid in contact therewith. The device includes a container that defines a cavity therein. A diaphragm within the container divides the cavity into two chambers on opposite sides of the diaphragm. The diaphragm prevents flow communication between the chambers A first fluid input means in flow communication with the first of the chambers introduces fluid to the first chamber. The first chamber has an acoustic compliance less than the mechanical compliance of the diaphragm. A second fluid input means is in flow communication with the second of the chambers for introducing fluid to that second chamber. Preferably, the second chamber has an acoustic compliance less than the mechanical compliance of the diaphragm. It is also preferred that the first fluid inlet comprise a conduit having a cylindrical bore in flow communication with the first chamber. It is also preferred that the device include a resilient member affixed to the diaphragm with means for adjusting the resilience of that resilient member.

BRIEF DESCRIPTION OF THE DRAWINGS

FIG. 9 is a diagram explanatory of the operation of the third embodiment of the present invention.

DESCRIPTION OF THE PREFERRED EMBODIMENTS

Figure 1:
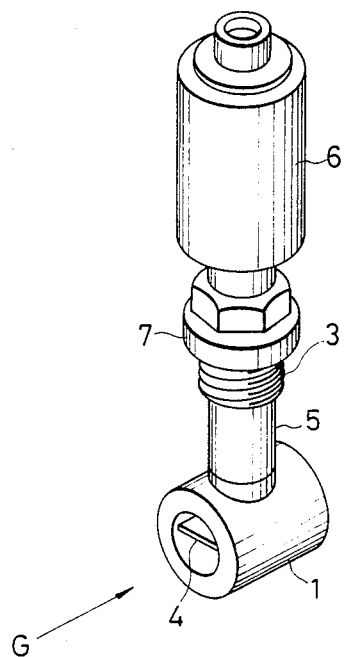
FIG. 1 is a perspective view of a conventional vibrating type transducer.
Figure 2:
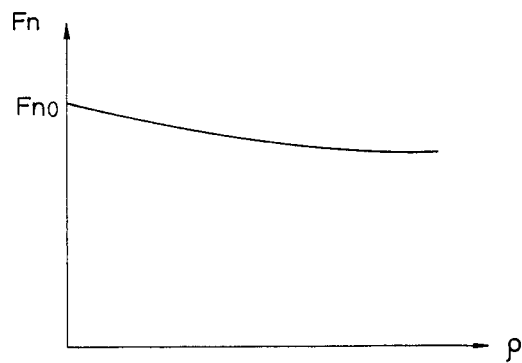
FIG. 2 is an operational diagram of the transducer of FIG. 1.

Referring now to the accompanying drawings, an embodiment of the present invention will be described in detail. In the drawings, like reference numbers or letters designate parts performing similar functions.

Figure 3:
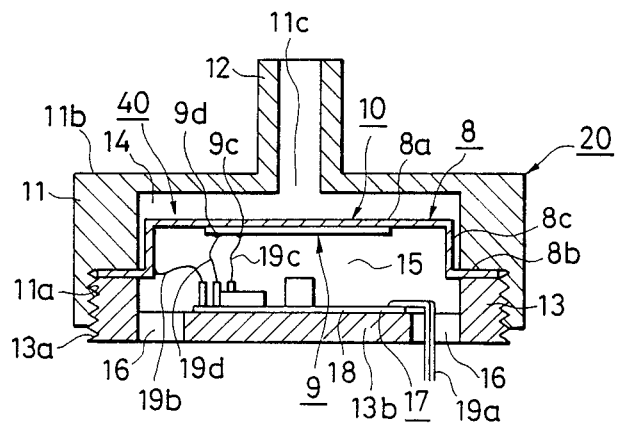
FIG. 3 is a vertical sectional view of a first embodiment of the present invention.
Figure 4:
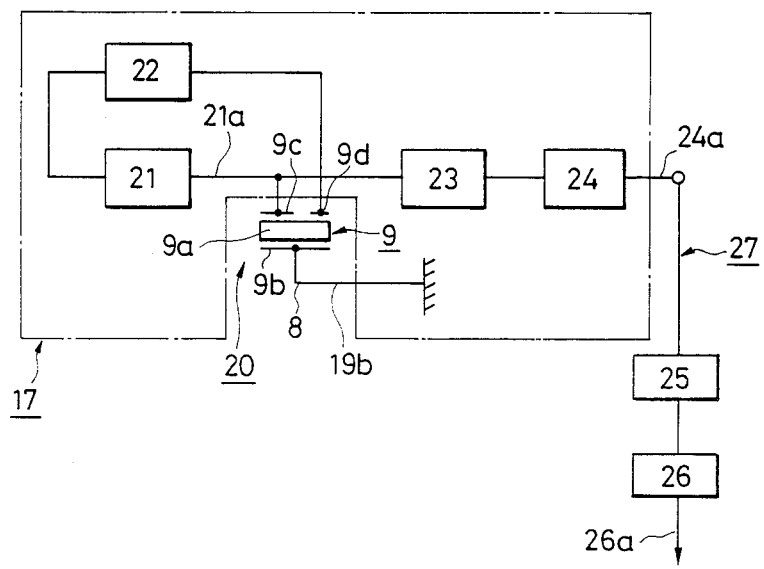
FIG. 4 is a block diagram of a detection circuit for driving the first embodiment.

FIG. 3 is a vertical cross-sectional view of an embodiment of the present invention, and FIG. 4 is a block diagram of a detection circuit used in the above embodiment. A closed-end cylindrical vibrating member 8 shown in FIGS. 3, 4 is provided with a piezo-electric vibrator 9 adhesively bonded to its inner bottom surface 8a. The vibrating body further includes a collar portion 8c and a flange portion 8b at its outer peripheral edge. The vibrating means 8 is formed from a metal sheet about 0.1 [mm] thick of kovar or 42 Ni-Fe alloy having a low thermal expansion coefficient. As shown schematically in FIG. 4 the piezo-electric vibrator 9 consists of a discoidal piezo-electric wafer 9a 0.1 0.2 mm thick. A first electrode 9b is formed on one side of the wafer 9a, a second electrode 9c and a third electrode 9d are formed on the other side thereof. That side on which the first electrode 9b is installed is affixed to the bottom surface 8a of the vibrating member 8 and connects the electrode 9b to the vibrating means 8 electrically. The vibrating member 8 and the piezo-electric vibrator 9 comprise the diaphragm 10. A container 11 is provided with internal threads 11a on the inner face on the open end side and one end of a cylindrical projection 12 is fixed to the surface 11b of the container 11 such that the cylindrical body 12 is coaxial with the container 11. A circular opening 11c through the projection 23 communicates with the inside of the container 11.

A closed-end cylindrical housing 13 is provided with external threads 13a on the outer side and, by screwing the external threads 13a into the internal threads 11a, the flange portions 8b of the vibrating member 8 is sandwiched in between the housing 11 and fixed in an inner cavity formed with the housing 13 and the container 11. A first cavity 14 is formed with the diaphragm 10 and the container 11, whereas a second cavity 15 is formed with the diaphragm 10 and the housing 13. Openings 16, 16 are formed in the bottom 13b of the housing 13 and a printed circuit board 18 forming a detection circuit 17 is bonded to the inner surface of the bottom 13b. The first cavity 14 is partitioned by the diaphragm 10 from the second cavity 15 in a fluid tight condition.

Conductors 19a are led out of the cavity 15 through the opening 16 to connect the detection circuit 17 to those outside the second cavity 15. Lead wires 19b, 19c, 19d connect the vibrating member 8 and the electrodes 9c, 9d of the piezo-electric vibrator 9 to the detection circuit 17, respectively. The vibrating means, here the diaphragm 10, the container 11 and the cylindrical projection 12 constitute a sensor 20.

The construction and operation of the detection circuit 17 will subsequently be described. An amplifier 21 applies output voltage to the piezo-electric wafer 9a through the electrode 9c and a feedback circuit 22 detects the voltage generated in the piezo-electric wafer 9a through the electrode 9d and positively feeds it back to the amplifier 21. The vibrating diaphagm 10 shown in FIGS. 3, 4 is constructed such that the piezo-electric wafer 9a expands and contracts in the radial direction when a.c. voltage is applied across the electrodes 9b, 9c. As a result the expansion and contraction of the piezo-electric wafer 9a causes the bottom 8a of the vibrating member 8 to vibrate in the axial direction of the cylindrical body. Consequently, a.c. voltage corresponding to the distortion of the piezo-electric wafer 9a is again generated across the electrodes 9d, 9b and the voltage is positively fed back to the amplifier 21 through the feedback circuit 22. Ultimately, the diaphragm continues the vibrating state in which it resonates at a natural frequency F through self-excited vibration.

An impedance conversion circuit 23 receives the output a.c. voltage 21a of the amplifier 21 having a frequency equal to the natural frequency F to facilitate the conversion of the voltage into a signal as described later. A waveform-shaping circuit 24 subjects the output signal of the converter circuit 23 to waveform shaping and outputs a signal 24a which is a pulse train of frequency F. The above-described amplifier 21, the feedback circuit 22, the impedance conversion circuit 23, the waveform-shaping circuit 24 and the printed circuit board 18 mounting these elements constitute the detection circuit 17.

A signal conversion circuit 25 receives the signal 24a and supplies a signal corresponding to the frequency F of the pulse train forming the signal to an operational means 26, which produces a density signal 26a by performing operations on the output signal of the signal conversion circuit based on an operational equation as described later on 25.

When the sensor shown in FIG. 3 is arranged in the fluid being monitored, the fluid being monitored is introduced into the cavity 14 through the cylindrical projection 12 and the cavity 15 through the openings 16. The diaphragm vibrates at the resonant frequency of what is termed the vibrating system 40 which consists of the first cavity 14 into which the fluid being monitored has been introduced, the opening 11c, the inside of the cylindrical projection 12 and the diaphragm 10 when the diaphragm 10 causes self-excited vibration. The frequency F of the pulse train of the output signal 24a produced by the waveform-shaping circuit 24 accordingly becomes equal to the resonant frequency of the vibrating system 40. The vibrator 9, the detection circuit 17 and the signal conversion circuit 25 constitute a frequency detector 27 shown in FIG. 4 for detecting the resonant frequency F of the vibrating system 40.

Referring to FIG. 5, the configuration of the vibrating diaphragm 10 will be described. As shown in FIG.

Figure 5A:
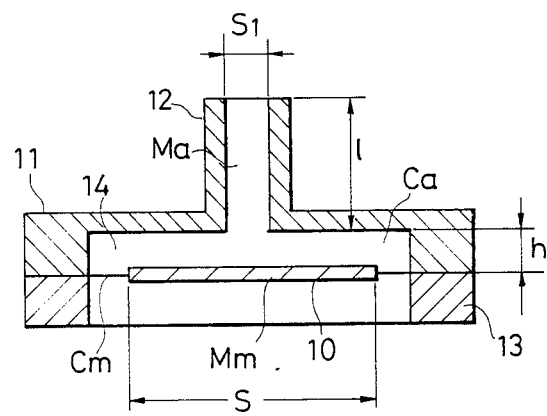
FIG. 5(A) is a typical diagram of the vibrating system.

3, the collar portion 8c of the vibrating member 8 is arranged opposite the inner side wall of the first cylindrical body 11 with an extremely narrow gap therebetween. The volume of the cavity 15 is significantly greater than that of the cavity 14 to make the pressure inside the cavity 15 almost nearly free from fluctuation even though the diaphragm 10 thus vibrates, so that the natural frequency of the cavity 15 is significantly lower than that of the vibrating system 40 composed of the diaphragm 10, the cavity 14, the opening 11c and the cavity inside the cylindrical projection 12. As a consequence, the principal components shown in FIG. 3 are represented by FIG. 5(A) in a typical form. FIG. 5(A) illustrates the mass Mm of the diaphragm 10, the area S of the bottom surface 8a of the vibrating member 8 and a mechanical compliance Cm proportional to the spring constant Km of the diaphragm 10, which establish a relationship given by Cm=1/Km, where Ma=mass of the fluid being monitored within the cylindrical projection 12; and Ca is expressed by Eq. (2).

$$Ca = W/(X^2 \cdot \rho) \ldots \quad (2)$$

where W=volume of the cavity 14; X=acoustic velocity in the fluid being monitored; and $\rho$=density of the fluid being monitored.

In FIG. 5(A), the height h of the cavity 14 and the sectional area $S_1$ of the bore of the cylindrical projection 12 are made extremely small to the extent that the principal parts are so arranged to allow the mass of the fluid being monitored in the cavity 14 and the acoustic volume within the bore of the cylindrical projection 12 to be negligible. Accordingly, the vibrating system constructed as shown in FIG. 5(A) is represented by an electrical equivalent circuit shown in FIG. 5(B) as the result of the conversion of the acoustic vibrating system consisting of the cavity 14 and the cavity within the bore of the cylindrical projection 12 into a mechanical vibrating system.

$$Mao = Ma \cdot (S^2/S_1^2) \quad (3)$$

$$Cao = Ca/S^2 \quad (4)$$

where Mao and Cao = mass and acoustic compliance given by Eqs. (3), (4), respectively.

Figure 5B:
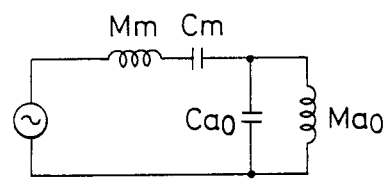
FIGS. 5(B), (C) are electric equivalent circuits of the vibrating system, respectively.
Figure 5C:
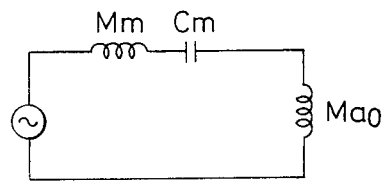
FIG. 5 is a drawing explanatory of the operation of the first embodiment of the present invention.

Assuming that Eq. (5) is established by setting the angular frequency of the vibration at $\omega$, FIG. 5(B) is rewritten as FIG. 5(C) and Eq. 6 is set up when the resonant frequency of the circuit of FIG. 5(C) is F.

$$|1/\omega \cdot Cao| \gg |\omega \cdot Mao| \quad (5)$$

$$F = \omega/2\pi \quad (6)$$

$$\omega = \sqrt{1/Cm \cdot Mn \cdot (1 + Mao/Mm)}$$

$$= \sqrt{1/Cm \cdot (Mm + Ma(S^2/S_1^2))}$$

Eq. (7) is obtained from Eqs. (3) (6).

$$1/(1+Mm/Mao) \cdot Cao/Cm \ll 1 \quad (7)$$

As is obvious from Eq. (6), the diaphragm 10 resonates at the frequency F if the principal components shown in FIG. 3 are so arranged as to establish the equivalent circuit of FIG. 5(C) and the frequency F of the pulse train forming the output signal 24a of the waveform-shaping circuit shown in FIG. 4 has a value corresponding to the mass Ma of the fluid being monitored in the cylindrical body 12. Accordingly, the density of the fluid being monitored can be obtained by determining the value of the frequency F. The operational circuit 26 performs operations based on Eq. (5) and outputs the density signal 26a equivalent to the density $\rho$ of the fluid being monitored. As shown in Eq. (6), the mass Ma changes as the density of the fluid being monitored changes and the resulting mass Ma affects the frequency F in such a manner as to enlarge the effect by $(S/S_1)^2$ times since the principal components are formed for satisfying $S/S_1 \gg 1$. Thus $(S/S_1)^2 \gg 1$. When the principal components of the device are adapted to set up the circuit of FIG. 5(C), the transducer shown in FIGS. 3, 5 is, as is apparent from the comparison between Eqs. (6), (1), capable of accurately monitoring fluid such as gas having a low density or compressive properties.

Figure 6:
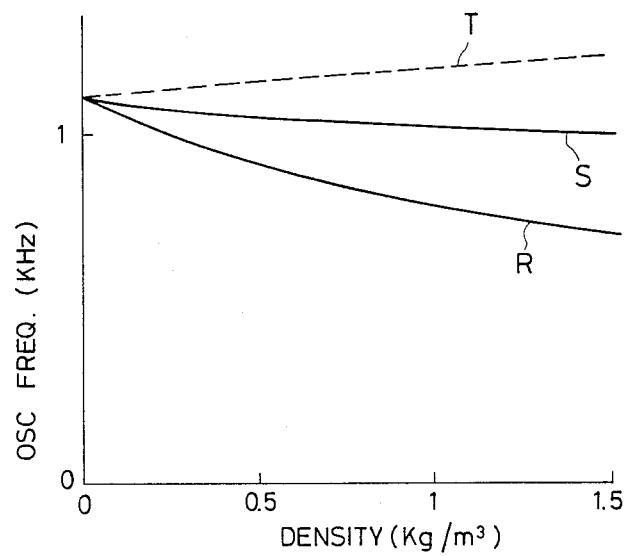
FIG. 6 is a plot showing density-frequency test results obtained from the first embodiment of the present invention.

As shown in FIG. 6, the principal components of the transducer shown in FIGS. 3, 4 is made up to set the value of Mao/Mm as large as possible to increase the slope of the frequency v. density curve and thus improve the measuring sensitivity. Accordingly, Eq. (8) is obtained from Eq. (7).

$$Cao/Cm \ll 1 \quad (8)$$

The above description is justifiable provided that Eq. (8) is valid. Eqs. (5) ~ (8) are therefore applicable because the principal components are adapted to increase the compliance Cm of the diaphragm 10 by forming the vibrating member 8 and the portion of the container adjacent to where the vibrating member 8 is sandwiched in between the container 11 and the housing 13, to make the acoustic compliance Cao of the cavity 14 significantly smaller than the compliance of the diaphragm 10 by minimizing the height h of the cavity 14, and maximizing Mao/Mm. In such a transducer, accordingly, the frequency of the pulse train represented by the equivalent circuit of FIG. 5(C) and forming the signal 24a of FIG. 4 becomes equal to F and, since $S/S_1 \gg 1$, the transducer will monitor a low density fluid such as gas with high sensitivity and accuracy. The frequency of the diaphragm 10 changes as the temperature of the fluid being checked changes but the effect of such a change on the measuring accuracy is less than that in case of the transducer of FIG. 1, so that the fluid can be monitored over a wide temperature range.

A characteristic line R shown in FIG. 6 reflects the test result when the sensor 20 of FIG. 3 is arranged to the satisfaction of all the above conditions. In FIG. 6, the resonant frequency is equal to the natural frequency of the vibrating system 40 consisting of the diaphragm 10, the first cavity 14, the opening 11c and the cavity within the cylindrical projection 12 or to the frequency of the pulse train forming the output signal 24a of the waveform-shaping Circuit shown in FIG. 4. Given a 0.05 [mm] thick plate as the vibrating member 8, a 24 [mm] outer diameter cylinder, a 0.5 [mm] high (h) cavity 14, a 3 [mm] inner diameter of the bore of the cylindrical projection 12 and that 15 [mm]long (l(shown in FIG. 5(A)) cylindrical projection 12, the characteristic line R holds. In this case, the compliance Cm of the diaphragm 10 is set at $0.51 \times 10^{-4}$ [m/N] and the acoustic compliance Cao of the cavity 14 at $6.3 \times 10^{-6}$ [m/N], whereby the conditions of Eq. (7) are met.

A characteristic line S represents the test result when the sensor 20 is so arranged to set the dimensions of the diaphragm 10 at the same values as those defined above and dispense with the cavity 14 and the bore of the cylindrical projection 12, i.e., when a transducer is constructed in a manner similar to what has been applied to the conventional one shown in FIG. 1. As shown in FIG. 6, the characteristic line S is slightly inclined, whereas the characteristic line R is steeply inclined. It is thus clear from FIG. 6 that the use of the sensor exhibiting the characteristic line R makes it easier to measure a low density as compared with the use of what has the characteristic line S. A characteristic line T of FIG. 6 shows the test result when a mechanical acoustic vibrating system such as a conventionally known piezo-electric vibrator wherein a container for making a cavity communicate with one side of the mechanical acoustic vibrating system, the container being provided with a simple opening. In such a vibrating system, the cavity formed therein is relatively large in size, so that the acoustic compliance of the cavity is large in contrast to the small compliance of the mechanical diaphragm rigidly formed. Consequently, the characteristic line T is inclined slightly up to the right. The mechanical acoustic vibrating system is therefore unusable for measuring the density as shown in FIG. 6.

Figure 7:
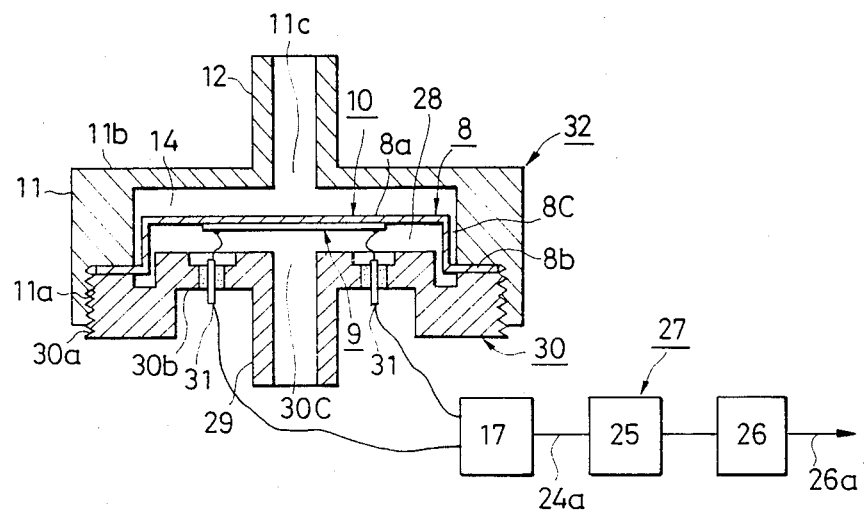
FIG. 7 is a vertical sectional view of a second embodiment of the present invention.

FIG. 7 is a vertical cross-sectional view of a portion corresponding to what is shown in FIG. 3 in a second embodiment of the present invention. What is different from the embodiment of FIG. 3 is that the embodiment of FIG. 7 includes a cavity 28 and a cylindrical body 29 respectively corresponding to the first cavity 14 and the cylindrical projection 12, however, the cavity 28 and the cylindrical projection 29 are provided on the side onto which the piezo-electric vibrator 9 is attached to the diaphragm 10. In this case, the bottom portion 30b of a housing 30 that forms the cavity 28 between the bottom portion and the diaphragm 10 is raised to minimize the thickness of the platelike cavity 28. Each electrode of the piezo-electric vibrator 9 is connected to the detection circuit 17 installed outside the cavities 28, 14 through a terminal 31 passed through the bottom 30b. One end of the cylindrical body 29 is fixed to the bottom 30b to allow the interior thereof to communicate with a opening 30c bored in the bottom 30b. A sensor 32 consists of the components shown in FIG. 7 excluding the detection circuit 17, the signal conversion circuit 25 and the operational means 26. Because the sensor 32 in FIG. 7 is thus constructed, the diaphragm 10 arranged in the fluid being monitored and caused to vibrate permits the sensor 32 to sense nearly the sum of the mass of the fluid in the cylindrical projection 29, whereas the mass of the fluid being monitored which vibrates as the diaphragm 10 vibrates, is almost equal to the mass of the fluid being monitored in the cylindrical projection 12 and sensed by the sensor 20 shown in FIG. 3, even though that mass is added to the mass of the diaphragm 10. As is apparent from Eq. (6), the use of the sensor 32 makes it possible to measure the density with sensitivity higher than that in the case of the sensor 20 of FIG. 3.

Although a description has been given of the application of the present invention to density measurement, the present invention is also applicable to pressure measurement. Although the above description refers to providing the container 11 with the cylindrical projection 12, and the housing 30 with the cylindrical projection 29, these cylindrical projections 12, 29 can be dispensed with, whereby the action of the fluid in the cylindrical projections 12, 29 can be replaced with that of the fluid in the openings 11c, 30c without problems.

Ma in Eq. (5) is expressed by Eq. (9).

$$Ma = \rho \cdot S_1 \cdot l \quad (9)$$

where l = length of the cylindrical projection 12; and, $\rho$ = density of the fluid being monitored. Accordingly, the density can be obtained from Eqs. 6, 9, provided that the frequency F is known.

The frequency F changes according to Eq. (6) in the transducer of FIG. 3 and it is obvious from Eqs. (6), (9) that the change of $\rho$ is $(S^2 \cdot l)/S_1$ times amplified to cause the change of F. In the transducer thus constructed, accordingly, the advantage is that highly sensitive measurement can be made possible by increasing $(S^2 \cdot l)/S_1$. In addition to that advantage, low density fluid such as gas can also be monitored by installing the cylindrical projection 12 offering greater $(S^2 \cdot l)/S_1$.

However, the cylindrical projection 12 thus installed causes acoustic resistance therein because of the viscosity of the fluid being checked and this phenomenon results in the reduction of Q of the vibrating system shown in FIG. 5(A), i.e., the vibrating system consisting of the diaphragm 10, the cavity 14 and the fluid being checked within the cylindrical projection 12. The reduced Q increases the acoustic resistance in the cylindrical projection 12 and makes it significant whenever an attempt is made to increase measuring sensitivity by increasing or decreasing $S_1$ of the cylindrical projection. In consequence, if it is attempted to increase measuring sensitivity in the transducer of FIG. 3, Q will be reduced, thus preventing the diaphragm 15 from causing stable self-excited vibration. Consequently, stable density measurement becomes impossible.

Figure 8:
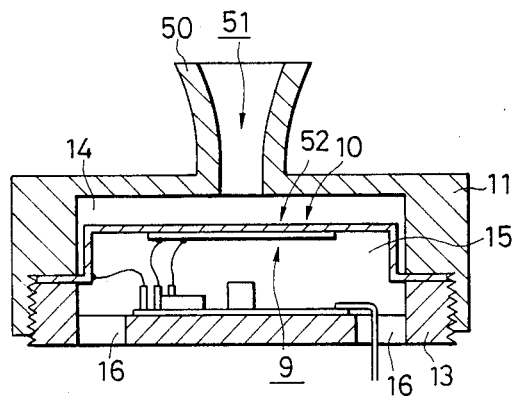
FIG. 8 is a vertical sectional view of a third embodiment of the present invention.

FIG. 8 is a vertical cross-sectional view of a third embodiment of the present invention wherein measures to counter the above problems posed in the first embodiment of FIG. 3 have been taken. In FIG. 8, there is installed a horn-shaped upper member 50 with one end attached to the container 11 instead of the straight-pipe-like cylindrical projection 12. The bore of upper member 50 is shaped like an exponential horn whose cross-sectional area varies exponentially with the sectional position.

Figure 9A:
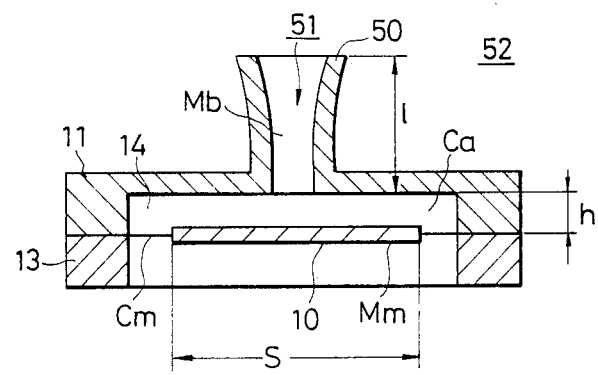
FIG. 9(A) is a typical diagram of the vibrating system.
Figure 9B:
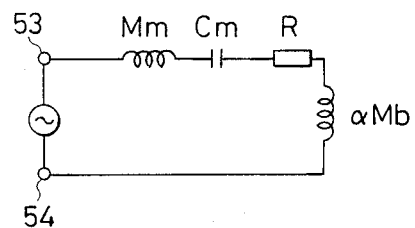
FIG. 9(B) is the electric equivalent circuit of the vibrating system.

Because the transducer of FIG. 8 is thus constructed, a signal 24a has a pulse train frequency equal to the resonant frequency of a vibrating system 52 compressed of the fluid being monitored in the cavity 14, the fluid contained in the opening in (the fluid in the member 50 and the cavity 14) hornlike upper member 50, the acoustic vibrating system 51 and the diaphragm 10 when the transducer is arranged in the fluid with its diaphragm 10 causing self-excited vibration. An electric equivalent circuit of the vibrating system 51 into a mechanical vibrating system as shown in FIG. 9(B). FIG. 9(A) is a typical drawing of the vibrating system 52 corresponding to FIG. 5(A) and, as shown in FIG. 5, the acoustic compliance Cao of the cavity 14 obtained from Eq. 4 is so arranged as to be significantly smaller than the mechanical compliance Cm of the diaphragm 10. In FIG. 9, the mass of the fluid being checked in the horn-like upper member 50 is expressed by Mb; a conversion factor for converting the acoustic impedance in the acoustic vibrating system 51 into that of the mechanical vibrating system by $\alpha$; and acoustic resistance in the acoustic vibrating system 51 with the thus converted impedence of the mechanical vibrating system by R. The vibrating system 52 is represented by the equivalent circuit of FIG. 9(B) in the vibrating type transducer of FIG. 8 and apparently the resonant frequency F1 of that circuit becomes what is defined by Eq. (10).

$$F_1 = \tfrac{1}{2}\pi \cdot \sqrt{1/Cm \cdot (Mm + \alpha Mb)} \quad (10)$$

Therefore, the frequency of the pulse train signal 24a produced by the detection circuit 17 becomes equal to $F_1$ and, in the transducer of FIG. 8, the density of the fluid being monitored can be measured by measuring the pulse frequency of the signal 24a. In the equivalent circuit of FIG. 9(B), the density measurement may be unstable as Q of the vibrating system 52 will be reduced if the resistance R has a large value. Since R in FIG. 9 is based on the acoustic resistance in the exponential horn-like upper member 50, however, the value R becomes substantially smaller than that in the case of the transducer of FIG. 3 whose cylindrical body is shaped like a straight pipe, below the cutoff frequency in the cylindrical body. Accordingly, Q of the vibrating system 52 shown in FIG. 9 becomes larger than Q of the corresponding vibrating system shown in FIG. 5(A) and the diaphragm 10 in the transducer of FIG. 8 is free from instability. This results in stable density measurement.

Figure 10:
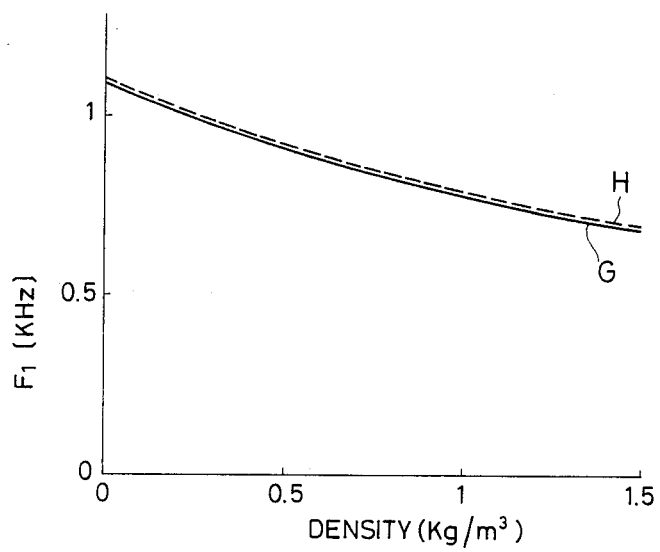
FIG. 10 is a plot showing density-frequency characteristic test results obtained from the third embodiment.

FIG. 10 displays test results obtained from the transducers of FIGS. 3, 8. FIG. 10 shows the relationship between the density of the fluid being monitored and the resonant frequency $F_1$ shown in Eq. (10), wherein G=characteristic line of the transducer of FIG. 8; H=characteristic line of the transducer of FIG. 3. FIG. 10 attests the fact that, even if the shape of the upper projection varies, the inclination of the characteristic line, i.e., density measuring sensitivity, can be equalized by properly increasing or decreasing the dimensions of the principal components.

Figure 11:
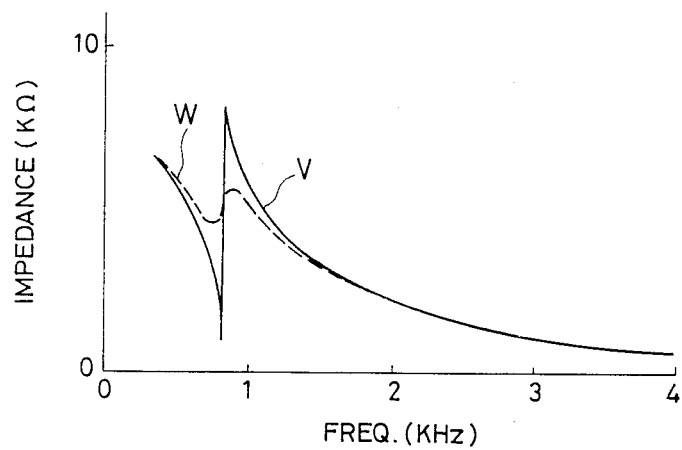
FIG. 11 is a plot showing frequency-impedance test results obtained from the third embodiment.

FIG. 11 shows other test results obtained from the transducers of FIGS. 3, 8. A characteristic line V in FIG. 11 indicates the relationship between the impedance and frequency when the resonance circuit side is viewed from power supply terminals 53, 54, whereas a characteristic line W represents the relationship between the corresponding impedance and the density in the case of the transducer of FIG. 3. The series and parallel resonance states still appear as the frequency changes in both the characteristic lines V, W because the static capacity across the driving electrodes in the piezo-electric vibrator 9 is connected to each resonant circuit in parallel in those tests. As is apparent from the drawings, however, the impedance changing mode in the characteristic line V is greater and steeper than that in the line W. According to the test results, Q of the vibrating system 52 in the transducer of FIG. 8 is larger than Q of the vibrating system of the transducer of FIG. 3. In the cases of FIGS. 10, 11, the adoption of the horn-like upper member 50 also makes available a vibrating type transducer allowing for stable measurement without reducing measuring sensitivity.

Figure 12:
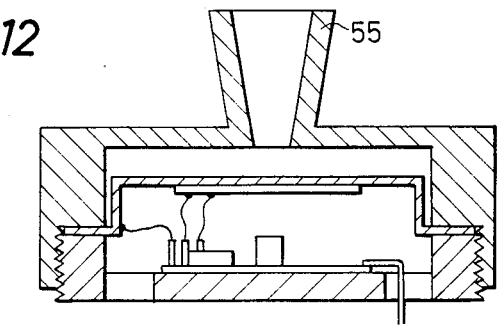
FIG. 12 is a vertical sectional view of a fourth embodiment of the present invention.

FIG. 12 is a vertical sectional view of a fourth embodiment of the present invention. The difference from what is shown in FIG. 8 is that an upper member 55 having a conical horn-like opening instead of the exponential horn-like upper member 50 is installed. Through tests, the present inventors have determined Q in the vibrating system employing such an upper member 55 becomes slightly smaller than that in the case of the upper member 50. The advantage is, however, that the transducer of FIG. 12 is readily constructed because the shape of the opening in the upper member 55 as compared with that of the upper member 50.

In the third and fourth embodiments, the acoustic vibrating system combined with the diaphragm 10, e.g., the vibrating system 51, is attached to one side of the diaphragm 10 but the arrangement thereof is not limited to the above examples according to the present invention. The acoustic vibrating system may be installed on both sides of the diaphragm and needless to say diaphragms, each having a horn-like opening for introducing fluid, may be arranged on both sides thereof in this case.

In the transducer shown in FIG. 3, both the mass Mn and compliance Cm of the diaphragm 10 vary with the shapes and dimensions of the vibrating member 8 and the piezo-electric vibrator 9 constituting the diaphragm. As is apparent from Eq. (6), each value of Mm, Cm therefore varies according to the transducer, thus causing a difference in performance among them.

Figure 13:
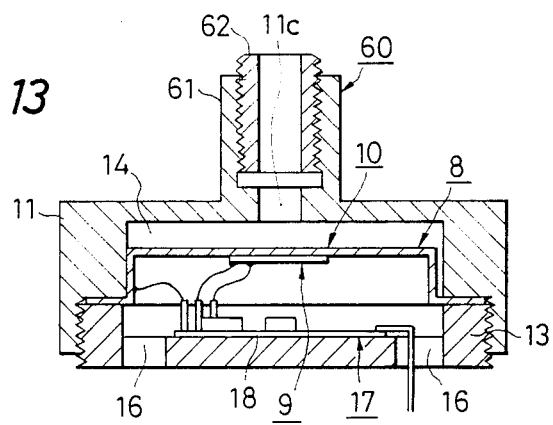
FIG. 13 is a vertical sectional view of a fifth embodiment of the present invention.

FIG. 13 is a vertical cross-sectional view of another embodiment of the present invention wherein measures to counter such variations have been taken into consideration. In this embodiment, a cylindrical upper member 60 for introducing the fluid being monitored into the container 11 through the opening 11c consists of an outer cylindrical body 61 having one end tightly fixed to the outer side of the container 11. The outer cylindrical body 61 includes internal threads formed on the inner surface, and an inner cylindrical body 62 is screwed into the outer cylindrical body.

As is apparent from Eq. 6, the frequency F changes as the mass Ma of the fluid being monitored in the cylindrical upper member 60 changes. When the diaphragm 10 does not resonate at the frequency corresponding to the given density of the fluid because there exists a difference in performance among transducers attributable to variations in Mm, Cm, it becomes possible to make the diaphragm 10 resonate at the given frequency by changing the mass Ma. In other words, the difference in performance among them can be nullified by changing the mass Ma, i.e., that difference in performance becomes readily eliminated in the case of the embodiment of FIG. 13 by adjusting the length of the inner cylindrical body 62 screwed into the outer cylindrical body 61 so as to sequentially change the mass Ma. When such a transducer is applied to the measurement of the intake air density of an internal combustion engine, it is possible to obtain a transducer free from differences in performance without minimizing variations in the mass Mm and compliance Cm. The resonant frequency F of the diaphragm 10 can conform to a given value by adjusting the position of the inner cylindrical body 62 while the internal-combustion engine is operated in the normal air condition at 20° C. and 760 mmHg.

Figure 14:
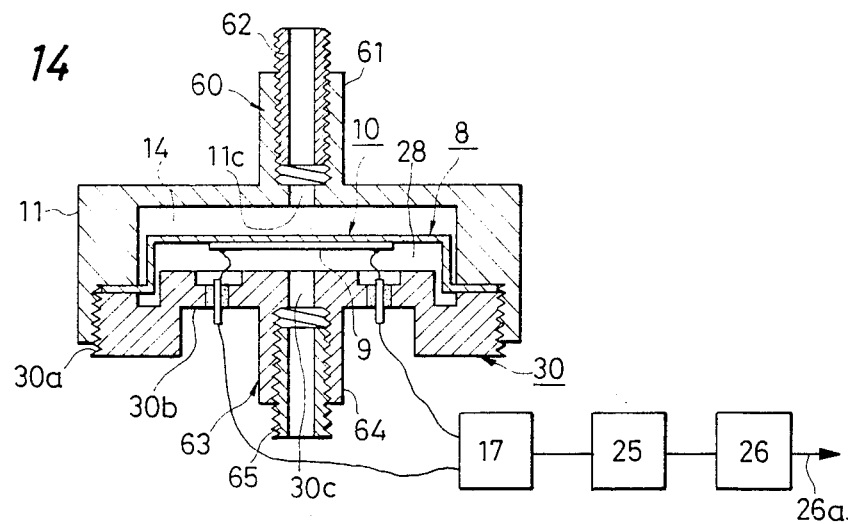
FIG. 14 is a vertical sectional view of a sixth embodiment of the present invention.

FIG. 14 is a vertical cross-sectional view of an additional embodiment of the present invention, which is similar in some respects to the embodiments of FIGS. 7 and 13. The difference between FIGS. 14 and 13 includes the configuration of the cavity 28 and a cylindrical lower 63 respectively corresponding to the cavity 28 and a cylindrical projection 29 of the embodiment of FIG. 7. As in the case of the example shown in FIG. 7, a closed-end cylindrical container 30 corresponding to the housing 13 of FIG. 13 forms the cavity 28 with the diaphragm 10. The housing 30 has a bottom 30b elevated close to the piezo-electric vibrator 9 to reduce the acoustic capacity of the cavity 28 by shortening the dimension between the bottom 30b and the diaphragm 10. Each electrode of the vibrator 9 is connected to a detection circuit arranged outside the cavities 28, 14 through a terminal 31 passed through the bottom 30b. The lower cylindrical body 63, as in the case of the upper cylindrical body 60 of the embodiment of FIG. 13, consists of an external cylindrical body 64 having one end fluid tightly fixed to the outer face of the bottom 30b of the container 30. The external cylindrical body has internal threads and an inner cylindrical body 65 is screwed into the external cylindrical body 64. The lower cylindrical body 63 is so arranged to introduce the fluid being monitored into the cavity 28 through a circular opening 30c provided in the bottom 30b, whereas the inner diameter of the inner cylindrical body 65 is equal to the diameter of the opening 30c. The difference in performance by types deriving from the above mass Mm and compliance Cm may be nullified using either cylindrical body 62 or 63.

Figure 15:
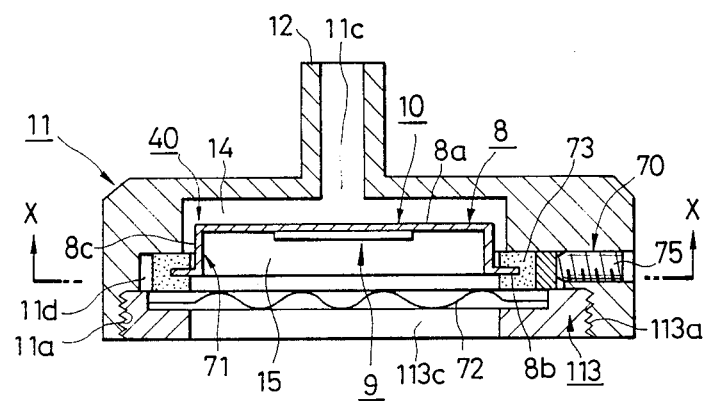
FIG. 15 is a vertical sectional view of a seventh embodiment of the present invention.
Figure 16:
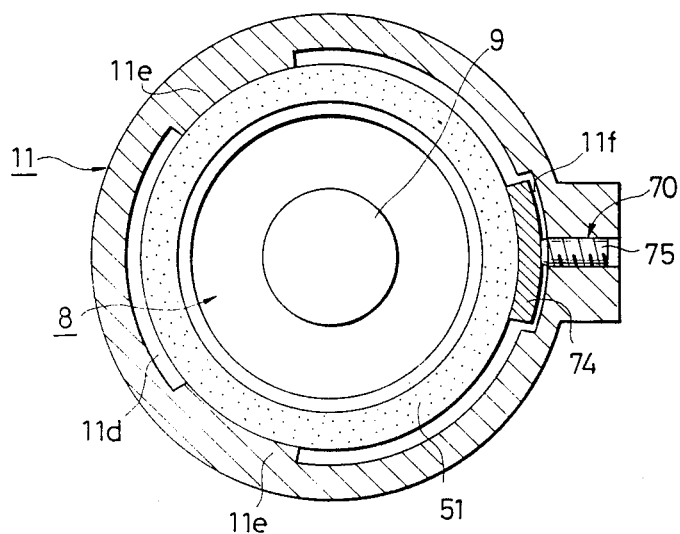
FIG. 16 is a sectional view taken on line X-X of FIG. 15.

FIG. 15 is a vertical cross-sectional view of a seventh embodiment of the present invention and FIG. 16 is a sectional view taken on line X—X of FIG. 15. In FIGS. 15, 16, the flange 8b of the vibrating member 8 is molded into a plastic ring-like frame 51 in one body. As in the case of each of the above embodiments, the closed-end cylindrical container 11 is provided with the internal thread 11a on the inner surface. The open end has a circular opening 11c within the cylindrical projection 12. The cylindrical projection 12 has one end fluid tightly fixed to the outer face of the bottom 11b of the container in such a manner as to make the cylindrical member 12 and the opening 11c concentric, the inner diameter of the former being equal to that of the latter. A circular step 11d is provided on the inner wall of the container 11 and a plurality of projections 11e are projected from the side wall having the stepped portion 11d.

A retainer 113 has external threads 113a its outer surface and a large diameter opening 113c in the bottom thereof. The retainer 113 contains a ring-like spring 72 having an alternate wave shape in the circumferential direction. The diaphragm 10 includes a frame 73 on its peripheral edge fixed to the container 11 as the frame 73 is pressed against the stepped portion 11d by spring 72 when the retainer 113 is screwed into the container 11 having the internal thread 11a. In other words, the vibrating member 8 is fixed to the housing 11 at the stepped portion 11d through the resilient support mechanism 71 consisting of the collar portion 8c of the vibrating means the flange portion 8b and the frame 73 of the vibrating member 8. A set screw 75 is used to press the frame 73 in the stepped portion 11d against the projections 11e from the side of the container 11 through an arcuate press member 74. A recess 11f is provided in the side wall of the stepped portion 11d to prevent the press member 74 from shifting in the circumference direction of the frame 73.

If the pressure applied by the set screw 75 to the frame 73 is deformed and this causes the curvature in the bottom surface 8a of the vibrating member toward the cavity 14 in a concave form. This causes the resilience of the resilient support mechanism to change. The compliance Cm of the diaphragm 10 consequently decreases, whereas the resonant frequency F according to Eq. (6) increases. Since the resonant frequency F may be changed by the set screw 75, the diaphragm 10 can be made to resonate at a given resonant frequency by changing the pressure applied by the set screw even though the initial difference in performance resulting from variations in Cm, Mm impedes the vibration of the diaphragm 10 in the transducer shown in FIGS. 15, 16 at a given frequency corresponding to a given fluid density. In other words, the difference in performance by types of transducer is easily nullified by adjusting the resilience of the resilient support mechanism 71 by the set screw 75, because the compliance Cm corresponds to the resilience of the resilient support mechanism 71. As a result, highly accurate measurement is possible without minimizing variations in the mass Mm and compliance Cm by specifically increasing the accuracy of the frequency measurement of the diaphragm 10. In FIG. 15, an adjustment means 70 for varying the resilience of the resilient support mechanism consists of the frame 73, the press member 74 and the set screw 75.

In the above-described seventh embodiment, the diaphragm is supported by the resilient support mechanism and the means for sequentially changing the resilience of the resilient support mechanism, so that the difference in performance because of variations in the mass of the diaphragm and the spring constant in the diaphragm support is readily nullified by changing the resilience of the resilient support mechanism using the resilience-varying means. Accordingly, a highly accurate vibrating-type transducer is readily available without specifically increasing the accuracy of the frequency measurement of the diaphragm.

Figure 17:
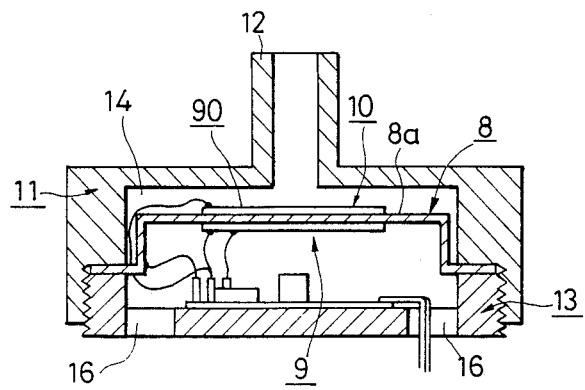
FIG. 17 is a vertical sectional view of an eighth embodiment of the present invention.
Figure 18:
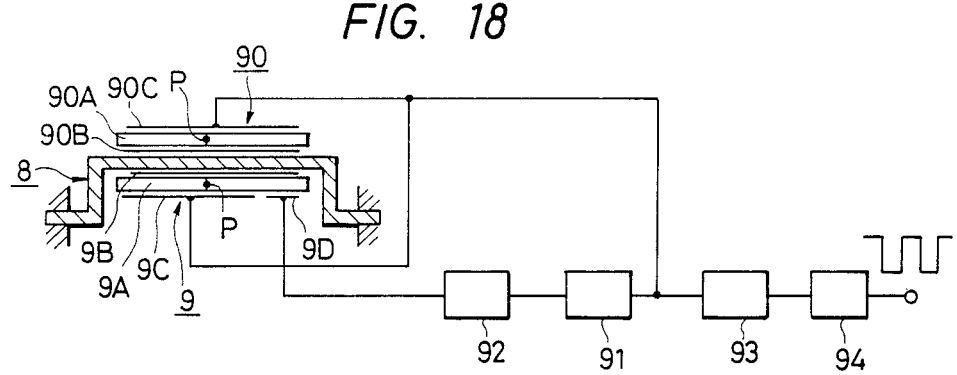
FIG. 18 is a schematic diagram showing the principal part of the eighth embodiment.

FIG. 17 is a vertical sectional view of an eighth embodiment of the present invention, whereas FIG. 18 is a drawing illustrative of the principal part of FIG. 17. In both FIGS. 17, 18, the vibrating member 8 is equipped with piezo-electric vibrators 9 and 90 that are adhesion-bonded onto both inner and outer surfaces of the bottom 8a thereof, respectively. The piezo-electric vibrator 90 consists of a discoidal piezo-electric wafer 90A prepared from PZT material, a first electrode 90B and a second electrode 90C connected to both sides of the wafer 90A, respectively. The piezo-electric vibrator 9 consists of a discoidal piezo-electric wafer 9A prepared from the same material and having the same dimensions as that and those of the wafer 90A. The first electrode 9B is connected to one side of the wafer 9A, a second electrode 9C and a third electrode 9D connected to the other side thereof. Both the vibrators 9, 90 are fixed to the vibrating member 8 in such a manner as to conductively connect the first electrodes 9B, 90B and the vibrating member 8. In this case, the wafers 9a, 90A allow the electrodes 9B, 90B to be oppositely polarized as shown by an arrow P of FIG. 18. Since member 8 and the vibrators 9, 90 are prepared from the above described materials the differences in the thermal expansion coefficient between them is extremely small.

The detection circuit will now be described. In- FIG. 18, an amplifier 91 applies output a.c. voltage to the piezo-electric wafers 9A, 90A through the electrodes 9C, 90C. A feedback circuit 92 detects the voltage generated in the piezo-electric wafer 9A through the electrode 9D and positively feeds it back to the amplifier 91. The diaphragm 10 is thus constructed as shown in FIGS. 17, 18, and includes the piezo-electric wafers 9A, 90A which expand and contract in the radial direction when the a.c. voltage is applied across the electrodes 90B, 90C and 9B, 9C. When the piezo-electric wafers 9A, 90A thus expand and contract, the bottom 8a of the vibrating member 8 vibrates in the axial direction of the cylindrical body. In other words, the wafer 9A contracts in the radial direction when the wafer 90A expands in the radial direction, whereas the wafer 9A expands when the wafer 90A contracts, and the bottom 8a of the vibrator member 8 vibrates as described above. Because the polarities of the piezo-electric wafers 9A, 90A and those of the voltages simultaneously applied to the piezo-electric wafers 9A, 90A are arranged as described above, when the wafer 9A thus expands and contracts, a.c. voltage corresponding to the expansion and contraction of the wafer 9A is generated and supplied to the feedback circuit 91 through the electrode 9D. The diaphragm 10 resonates at the natural frequency F thereof and continues self-excited vibration because the output of the circuit is positively fed back to the amplifier 91. An impedance conversion circuit 93 receives output a.c. voltage having a frequency equal to the frequency F, whereas a waveform shaping circuit 94 shapes the waveform of the output signal of the conversion circuit 93 and supplies a pulse train signal of frequency F.

In the vibrating type transducer of FIG. 3, the physical properties of each material vary and although materials forming the vibrating member 8 and the vibrator 9 are selected as to minimize the difference between their thermal expansion coefficients, it is difficult to make the value of the difference therebetween small or keep it at zero over a wide range of operating temperatures. In consequence, the diaphragm 10 of FIG. 3 may warp depending on the temperature at which the transducer of FIG. 3 is operated and cause a measuring error to be produced, whereas the diaphragm 10 in the transducer shown in FIGS. 17, 18 will not warp over a wide range of operating temperatures because the vibrators 9, 90 equal in dimensions and materials are respectively bonded on both sides of the vibrating member 8. For this reason, such a transducer allows measurement with the least measuring error over a wide range of operating temperatures. In this case, the difference between thermal deformations resulting from the difference between the thermal expansion coefficients of the vibrating member 8 and the vibrators 9, 90 is absorbed by the adhesive sandwiched in between the vibrating member and the vibrators.

Figure 19:
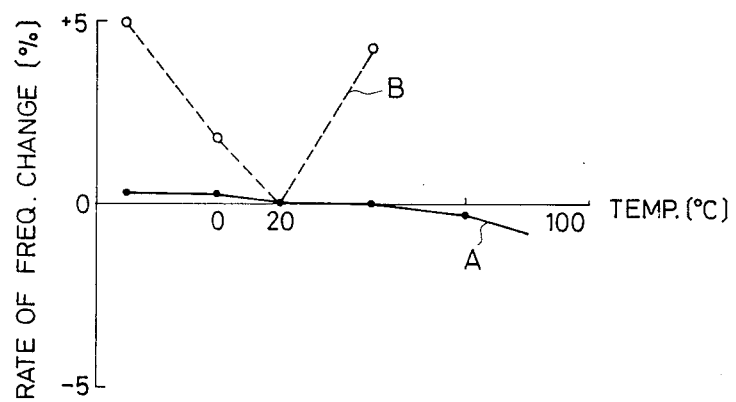
FIG. 19 is a plot showing temperature-rate of frequency change test results obtained from the eighth embodiment.

FIG. 19 is a graph illustrating the result obtained from a test of the transducer shown in FIGS. 17, 18, wherein the line A represents a rate of change of the frequency of the pulse train signal appearing when the temperature of the fluid being monitored is changed. In FIG. 19, the test result obtained from the embodiment of FIG. 3 is also shown as the line B for the purpose of comparison. As shown in FIG. 19, the temperature characteristics derived from the eighth embodiment of FIG. 17 have been much improved as compared with that of the first embodiment of FIG. 3.

The vibrator 9 or 90 formed on one side of the bottom 8a of the vibrating member 8 may be a pseudo-vibrator equal in dimensions and material to the vibrator 9 or 90 and bonded onto the other side thereof to constitute the diaphragm. This pseudo-vibrator is a disk without piezo-electric properties and electrodes. In the diaphragm thus formed, the effects of thermal expansion of the vibrator 9 or 90 and the pseudo-vibrator become equal. It is accordingly apparent that a transducer producing the least measuring error over a wide range of operating temperatures is obtainable as in the case of FIG. 17.

As set forth above, according to the present invention a cavity is formed on at least one side of and opposite to the diaphragm but prevented from communicating with the other side thereof. The acoustic vibrating system having a cylindrical body for leading the fluid being monitored to the cavity is provided and the acoustic compliance of the cavity is set smaller than the mechanical compliance of the diaphragm.

In the present invention, accordingly, the action of the fluid being monitored is tantamount to increasing the mass of the vibrating system including the diaphragm. While the diaphragm vibrates its vibration is boosted by the interaction of the cavity and the cylindrical body, whereby the transducer thus constructed is capable of accurately monitoring gas over a wide range of operating temperatures.

According to one preferred embodiment of the present invention, acoustic resistance within the cylindrical projection reduced since the projection for introducing the fluid being monitored into the cavity is horn-shaped and Q of the vibrating system consisting of the diaphragm, the cavity and the fluid within the cylindrical projection is prevented from decreasing, so that stable measurement becomes possible.

According to another preferred embodiment of the present invention, even though variations in the mass of the diaphragm and the spring constant exist, the difference in performance by different types of transducers because of such variations is nullified by varying the length of the cylindrical projection leading the fluid being monitored to the cavity. Consequently, a vibrating type transducer permitting accurate measurement is obtained without specifically increasing diaphragm processing accuracy.

According to still another preferred embodiment of the present invention, even though variations in the mass of the diaphragm and the spring constant exist, the difference in performance because of the variations is nullified by changing the resilience of the resilient support mechanism. Consequently, a vibrating type transducer permitting accurate measurement is provided without specifically increasing diaphragm processing accuracy.

According to another preferred embodiment of the present invention, even though there is a difference in the thermal expansion coefficient between the vibrating means and the vibrator, the vibrating means or vibrator will not warp as the temperature fluctuates because the piezo-electric vibrators are respectively coupled to the diaphragm on both sides of the direction of flexural vibration. Alternatively piezo-electric vibrator is coupled to the diaphragm on one side of but a pseudo-vibrator is coupled thereto on the other side thereof, the piezo-electric vibrator and the pseudo-vibrator being so arranged as to have an equal effect of thermal expansion on the vibrating means. Consequently, measurement with minimum error can be implemented over a wide range of operating temperatures.

The present invention has been disclosed in terms of preferred embodiments, however, the scope of the invention is not limited thereto. The scope of the invention is determined by the appended claims and their equivalents.

What is claimed is:

1. A device to aid in detecting the resonant frequency of a diaphragm to measure properties of a fluid in contact therewith, said device comprising:
   a container defining a cavity therein;
   a diaphragm within said cavity, said diaphragm dividing said cavity into two chambers on opposite sides of said diaphragm, said diaphragm preventing flow communication between said chambers;

first fluid inlet means in flow communication with a first of said chambers for introducing said fluid to said first chamber, said first chamber having an acoustic compliance less than the mechanical compliance of said diaphragm, said first fluid inlet means including a conduit having a convergent bore; and second fluid inlet means in flow communication with a second of said chambers for introducing fluid to said second chamber.

2. The device of claim 1, wherein the shape of said bore is exponential.

3. The device of claim 1, wherein the shape of said bore is conical.

* * * * *